(12) United States Patent
Fraas et al.

(10) Patent No.: US 10,589,034 B2
(45) Date of Patent: Mar. 17, 2020

(54) SAFETY DEVICE FOR A SYRINGE

(71) Applicant: Gerresheimer Regensburg GmbH, Regensburg (DE)

(72) Inventors: Andreas Fraas, Amberg (DE); Maximilian Vogl, Mantel (DE)

(73) Assignee: Gerresheimer Regensburg GmbH, Regensburg (DE)

( * ) Notice: Subject to any disclaimer, the term of this patent is extended or adjusted under 35 U.S.C. 154(b) by 27 days.

(21) Appl. No.: 15/573,038

(22) PCT Filed: Jun. 9, 2016

(86) PCT No.: PCT/EP2016/063116
§ 371 (c)(1),
(2) Date: Nov. 9, 2017

(87) PCT Pub. No.: WO2016/202670
PCT Pub. Date: Dec. 22, 2016

(65) Prior Publication Data
US 2018/0161511 A1    Jun. 14, 2018

(30) Foreign Application Priority Data
Jun. 15, 2015   (EP) ..................................... 15172165

(51) Int. Cl.
*A61M 5/32* (2006.01)
*A61M 5/31* (2006.01)
*A61M 5/34* (2006.01)

(52) U.S. Cl.
CPC ........ *A61M 5/3202* (2013.01); *A61M 5/3134* (2013.01); *A61M 5/326* (2013.01);
(Continued)

(58) Field of Classification Search
CPC .. A61M 5/3272; A61M 5/3271; A61M 5/326; A61M 2005/3267
See application file for complete search history.

(56) References Cited

U.S. PATENT DOCUMENTS 2,695,613 A   2/1953  John
2,834,346 A   6/1955  Adams
(Continued)

FOREIGN PATENT DOCUMENTS

DE   11 2009 001 083 T5   3/2011
EP        1 797 857 A1    6/2007
(Continued)

OTHER PUBLICATIONS

Canadian First Office Action, dated Sep. 17, 2018 in Canadian Patent Application No. 2,984,475, a related application, 3 pp.
(Continued)

*Primary Examiner* — Nathan R Price
*Assistant Examiner* — Melissa A Snyder
(74) *Attorney, Agent, or Firm* — Leydig, Voit & Mayer, Ltd.

(57) ABSTRACT

The invention relates to a safety device for avoiding stabbing injuries, for a syringe having a syringe body and a piercing means arranged on the distal end of said syringe body. The safety device comprises a sleeve element that extends in an axial direction (X) and encloses at least partly the piercing means and the syringe body, and a collar element that is arranged on a distal end region of the syringe body and locks the safety device in the axial direction (X), said collar element having at least one guide projection which is guided in at least one guide track of the sleeve element during a movement of the syringe body relative to the sleeve element substantially in the axial direction. The safety device is characterised in that the collar element is arranged on the distal end region of the syringe body so as to be rotatable in a circumferential direction (U) and has at least one tolerance compensating element which is in operative contact, mechanically, with the syringe body so that tolerances of the syringe body can be compensated for.

20 Claims, 6 Drawing Sheets

(52) U.S. Cl.
CPC ........ *A61M 5/3243* (2013.01); *A61M 5/3272* (2013.01); *A61M 5/343* (2013.01); *A61M 5/348* (2013.01); *A61M 2005/3253* (2013.01); *A61M 2005/3267* (2013.01)

(56) References Cited

U.S. PATENT DOCUMENTS

| | | | |
|---|---|---|---|
| 5,595,566 | A | 1/1997 | Vallelunga et al. |
| 5,611,786 | A | 3/1997 | Kirchhofer et al. |
| 5,843,041 | A | 12/1998 | Hake et al. |
| 7,850,027 | B2 * | 12/2010 | Hayes ................ A61J 9/00 206/219 |
| 8,425,460 | B2 * | 4/2013 | Cowe ................ A61M 5/326 604/110 |
| 2004/0186443 | A1 | 9/2004 | Covino et al. |
| 2005/0222539 | A1 * | 10/2005 | Gonzales ........ A61M 5/2033 604/207 |
| 2013/0281970 | A1 | 10/2013 | Erickson et al. |
| 2014/0039407 | A1 * | 2/2014 | Schoonmaker ..... A61M 5/3202 604/198 |
| 2014/0257337 | A1 * | 9/2014 | Oster ............... A61M 25/02 606/138 |
| 2016/0015905 | A1 | 1/2016 | Fournier et al. |
| 2018/0104421 | A1 | 4/2018 | Wittland et al. |
| 2018/0110934 | A1 | 4/2018 | Wittland et al. |
| 2018/0133409 | A1 | 5/2018 | Fraas et al. |
| 2018/0161512 | A1 | 6/2018 | Wittland et al. |
| 2018/0161516 | A1 | 6/2018 | Wittland et al. |

FOREIGN PATENT DOCUMENTS

| | | |
|---|---|---|
| EP | 1 949 929 A1 | 7/2008 |
| EP | 2 572 745 A1 | 3/2013 |
| WO | WO 1995/001812 A1 | 1/1995 |
| WO | WO 2003/018092 A1 | 3/2003 |
| WO | WO 2003/047657 A2 | 6/2003 |
| WO | WO 2009/137845 A1 | 11/2009 |
| WO | WO 2013/134465 A1 | 9/2013 |
| WO | WO 2014/131985 A1 | 9/2014 |
| WO | WO 2016/120185 A2 | 8/2016 |

OTHER PUBLICATIONS

International Search Report with Written Opinion corresponding to International Patent Application No. PCT/EP2016/063116, dated Oct. 14, 2016, 16 pgs.

Office Action corresponding to European Patent Application No. 15172165.1, dated Nov. 20, 2017, 5 pgs.—Search results on p. 3 only.

Canadian Office Action, dated Apr. 24, 2019, in Canadian Patent Application No. 2,984,475, application with related technology and inventor in common, 1 pp.

* cited by examiner

SAFETY DEVICE FOR A SYRINGE

CROSS-REFERENCE TO RELATED APPLICATIONS

This application is a U.S. National Stage Application under 35 U.S.C. § 371 of International Application No. PCT/EP2016/063116, filed Jun. 9, 2016, which claims the benefit and priority of European Patent Application No. 15172165.1, filed Jun. 15, 2015, both of which are hereby incorporated by reference in their entirety to the extent not inconsistent herewith.

The invention relates to a safety device for avoiding stabwounds for a syringe having a syringe body and a piercing means arranged at the distal end of the syringe body, comprising a sleeve element, which extends along an axial direction (X) and at least partially encloses the piercing means and the syringe body, and a collar element, which is arranged on the distal end of the syringe body and locks the safety device in the axial direction (X), the collar element comprising at least one guide projection, which is guided in at least one guide track of the sleeve element, substantially in the axial direction, when the syringe body is moved relative to the safety device.

Generic safety devices for avoiding stabwounds are known from the prior art. The use of safety devices of this kind is meaningful in particular in the case of pre-filled syringes. The handling of such syringes is very simple, as the medium does not have to be transferred into the syringe prior to application. Furthermore, the likelihood of using an incorrect medicine is very low, even in emergencies. For vaccines and countless other medicines they are now the first-choice primary packaging material. These syringes are usually manufactured from glass or plastics material (for example COC, COP) and need to be equipped with protective caps in order to prevent damage to and/or contamination of the cannula before the syringe is used. Moreover, it is important to secure the cannula after the syringe has been used, in order to avoid stab wounds. In this case, careless replacement of the protective cap on the cannula can cause stab wounds. Often, the corresponding protective cap can no longer be found, or replacement of said cap is forgotten, which results in an avoidable risk of injury.

Accordingly, needle guards have been developed that are rigidly connected to the syringe and automatically receive the needle again after the syringe has been used. A needle guard of this kind is disclosed in DE 11 2009 001 083 T5 for example. Said document discloses a spring-driven safety sleeve which, when extended, surrounds the cannula and prevents said cannula from causing injury to the user. The safety sleeve has a curved track in which at least one guide pin moves, as a result of which it is possible to achieve different positions of the safety sleeve according to the needle tip.

In this case, the at least one guide pin has to be fastened to the front geometry of the syringe by means of a collar, or has to be rigidly connected to the syringe in another manner. In order to prevent tampering or incorrect use, it should not be possible, or it should be possible only with difficulty, to remove the collar comprising the guide pin from the syringe comprising a cannula. Accordingly, a correspondingly secure fit in the axial direction is necessary.

This results in the problem that, when there is a secured guide pin, the safety sleeve undergoes some degree of rotation about the longitudinal axis of the syringe body on account of the curved track. The resulting rotation of the safety sleeve located on the patient's skin is perceived by the patient as uncomfortable, since the rotation of the safety sleeve twists the skin around the puncture site.

It is, however, difficult to achieve rotation of a collar comprising a guide pin that is reliable and simultaneously smooth, since in particular the vital front region is formed very imprecisely, in particular in the case of glass syringes, and/or different manufacturers produce different designs of the front geometry in the case of plastics syringes.

The object of the present invention is that of providing a safety device for avoiding stab wounds for a syringe, which solves the problems mentioned at the outset.

This object is achieved by a safety device for avoiding stab wounds for a syringe having a syringe body and a piercing means arranged at the distal end of the syringe body, comprising a sleeve element, which extends along an axial direction (X) and at least partially encloses the piercing means and the syringe body, and a collar element, which is arranged on a distal end region of the syringe body and locks the safety device in the axial direction (X), the collar element comprising at least one guide projection, which is guided in at least one guide track of the sleeve element, substantially in the axial direction, when the syringe body is moved relative to the sleeve element. The safety device is characterised in that the collar element is arranged on the distal end region of the syringe body so as to be rotatable in a circumferential direction (U) and has at least one tolerance compensating element which is in operative contact, mechanically, with the syringe body so that tolerances of the syringe body can be compensated for.

When the syringe is being used, the syringe, together with the safety device, is pressed against the patient's skin. The movement of the syringe body relative to the sleeve element and the guidance of the guide projection in the guide track, cause the collar element to rotate in a circumferential direction (U). The sleeve element thus preferably slides over the syringe body, as a result of which the piercing means, which may be a cannula, a needle or a lancet, passes through a corresponding opening in the sleeve element. Rotation of the sleeve element on the patient's skin, about the puncture site, is thus prevented.

Furthermore, the at least one tolerance compensating element compensates for occurring tolerances of the syringe body at the distal end region thereof, which region can also be referred to as the syringe front geometry. In this case, tolerances are understood as a deviation in the shape and/or the dimensions of the syringe body from the ideal shape or the ideal dimensions in this distal end region. In the case of glass syringes, tolerances of this kind may occur during manufacture. Tolerances of this kind can also result from differing shapes of the syringe front geometry in the case of syringes from different manufacturers. Tolerances of this kind can comprise, for example, the diameter of the syringe front geometry, the length of the syringe front geometry, or irregularities in the rounding of the syringe front geometry. In order to ensure optimal smooth guidance of the guide projection in the guide track, it is necessary for the collar element to be in an ideal assembly position. Even the slightest of deviations from this position can impair the guidance. Such tolerances of the syringe body can now be compensated for by the at least one tolerance compensating element, which is in operative contact, mechanically, with the syringe body. It is thus possible to achieve precise positioning of the collar element on the syringe body, which in turn results in optimal guidance of the guide projection in the guide track. Moreover, use of the safety device for different designs of the front geometry in the case of plastics syringes from different manufacturers is also made possible.

According to a particularly preferred embodiment, the collar element is substantially formed as a hollow circular cylinder. Preferably, the circular cylinder comprises a lateral surface, on which the at least one guide projection is arranged. Preferably, the at least one guide projection extends radially away from the lateral surface. Further preferably, the guide projection is formed as a circular cylinder or as a pin. Advantageously, two diametrically opposed guide projections are arranged on the lateral surface. Accordingly, the sleeve element would also comprise two diametrically opposed guide tracks, in each of which a guide projection is guided.

The syringe body is preferably designed as a hollow circular cylinder and has in its distal end region a conical end piece on which the piercing means is arranged. Preferably, a projection is formed on the conical end piece, with which projection a front face of the distal end of the collar element can engage, as a result of which the collar element, and thus the safety device, can be locked in the axial direction.

According to a particularly preferred concept of the invention, the at least one tolerance compensating element protrudes beyond a distal end of the collar element along the axial direction (X). An embodiment of this kind ensures ideal positioning of the collar element in the axial direction.

According to a further particularly preferred concept of the invention, the at least one tolerance compensating element extends from the collar element, along a radial direction (R), inwards to the syringe body. An embodiment of this kind ensures ideal positioning of the collar element in the radial direction.

The at least one tolerance compensating element is preferably punch-like. In this case, the punch-like tolerance compensating element preferably comprises a contact surface which can be brought into operative contact with the syringe body. This contact surface preferably has small dimensions, preferably between 0.5 mm$^2$ and 5 mm$^2$, and particularly preferably between 0.5 mm$^2$ and 1.5 mm$^2$, so as to reduce the friction between the collar element and the syringe body during rotation of the collar element.

The at least one tolerance compensating element is preferably resilient. The tolerances of the syringe body that may occur can thus be compensated for by deformation of the at least one tolerance compensating element.

According to a particularly preferred embodiment, the collar element comprises three tolerance compensating elements. The tolerance compensating elements are preferably arranged on the distal end of the collar element such that two central axes of the tolerance compensating elements enclose an angle ($\alpha$, $\beta$, $\gamma$) in each case. The angles are preferably $\alpha=\beta=\gamma=120°$. It is also conceivable, however, for different angles to be enclosed by the corresponding central axes. An embodiment of this kind makes it possible in particular to prevent a tilted position of the collar element on the syringe body.

The at least one tolerance compensating element is preferably formed integrally with the collar element. A collar element of this kind is particularly simple and cost-effective to produce. It is also conceivable, however, for the collar element to comprise at least one recess in the wall region thereof, in which recess at least one tolerance compensating element can be arranged. An embodiment of this kind makes it possible to produce the at least one tolerance compensating element and the collar element from different materials.

According to a preferred embodiment, the collar element comprises a distal region in which the wall of the collar element comprises at least two slots that extend in the axial direction (X). Slots of this kind make it possible to adapt the collar element to different syringe body shapes and/or syringe body diameters. Furthermore, the slots make it easier to attach the collar element to the syringe body. When attaching the collar element to the syringe body, the collar element is usually pushed onto the syringe body. If the syringe body comprises a projection or a thicker portion, which may be used for locking the collar element in the axial direction for example, attachment may become more difficult. However, the advantageous slots allow the collar element to be widened a small amount, with the result that said element can be pushed onto the syringe body more easily.

The collar element preferably comprises a proximal region that has an inside taper. This proximal region provides a second bearing point for the collar element on the syringe body, in the region of the syringe shoulders.

At least one element that protrudes inwards in the radial direction is preferably arranged at least in the proximal region of the collar element. The protruding element advantageously extends from the collar element, in a radial direction, inwards to the syringe body. This at least one protruding element reduces the contact surface of the collar element on the syringe body, which also reduces the friction between the collar element and the syringe body during a rotation of the collar element. Particularly preferably, three protruding elements are arranged in the proximal region of the collar element, which ensures optimal mounting of the collar element on the syringe body.

The safety device preferably comprises at least one spring element, which is operatively connected to the syringe body and counteracts the movement of the syringe body relative to the safety device. Accordingly, the cannula remains inside the sleeve element until the intended use. During use, the sleeve element has to be moved counter to the spring force in order for the cannula to be able to pass through the opening of the sleeve element. After the syringe has been used, the sleeve element automatically slides over the cannula again, driven by the spring force of the spring element. The guidance of the guide projection in the guide track causes the collar element to rotate counter to the circumferential direction (U). The user is thus protected from receiving stab wounds from the used contaminated cannula. The spring element preferably comprises a spiral spring. Other types, however, of spring are also conceivable, such as leg springs or torsion springs. It would furthermore be conceivable to form the spring element as an elastomer.

The collar element and/or the at least one tolerance compensating element preferably consist of slip-modified polyoxymethylene (POM) or of a silicone compound, which again makes it possible to reduce the friction between the collar element and the syringe body during rotation of the collar element.

The collar element and/or the at least one tolerance compensating element preferably comprise a glide-enhancing coating.

Other advantages, aims and properties of the present invention are explained with reference to the following description of the attached drawings. Similar components can have the same reference signs in the various embodiments.

Figure 4:
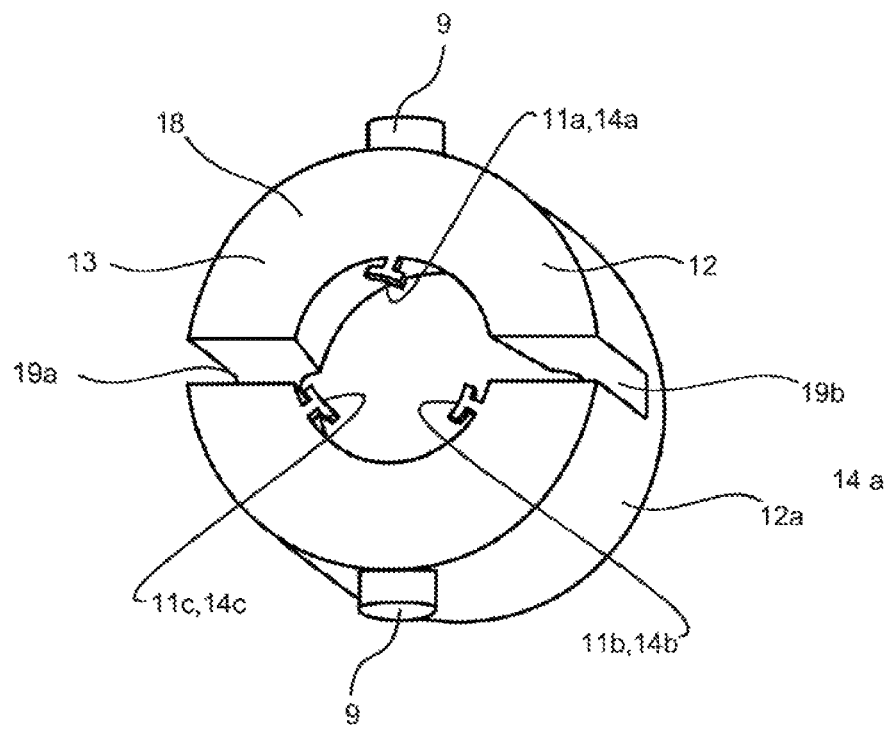
Figure 5:
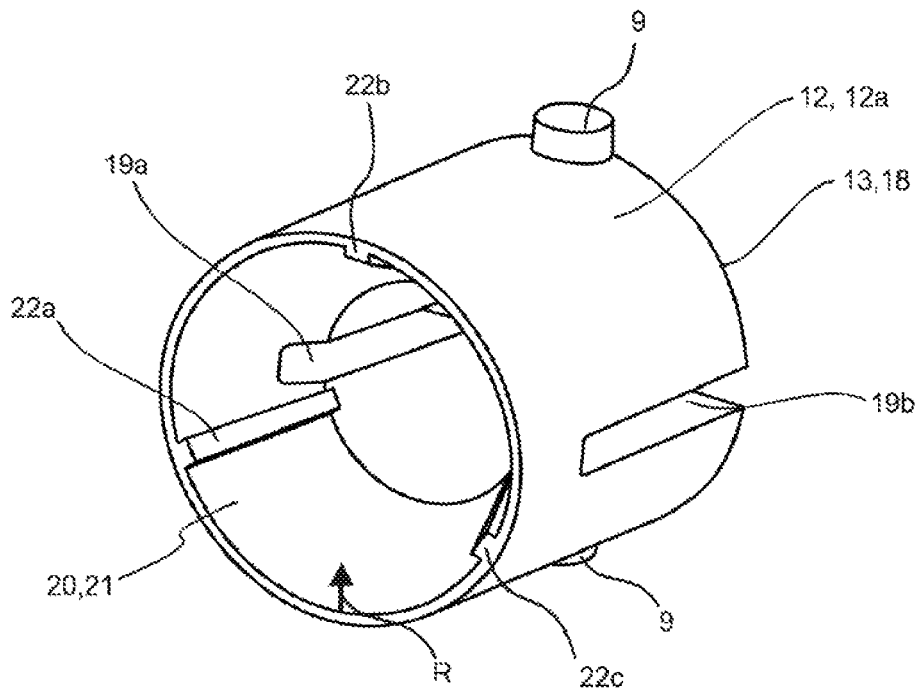
Figure 6:
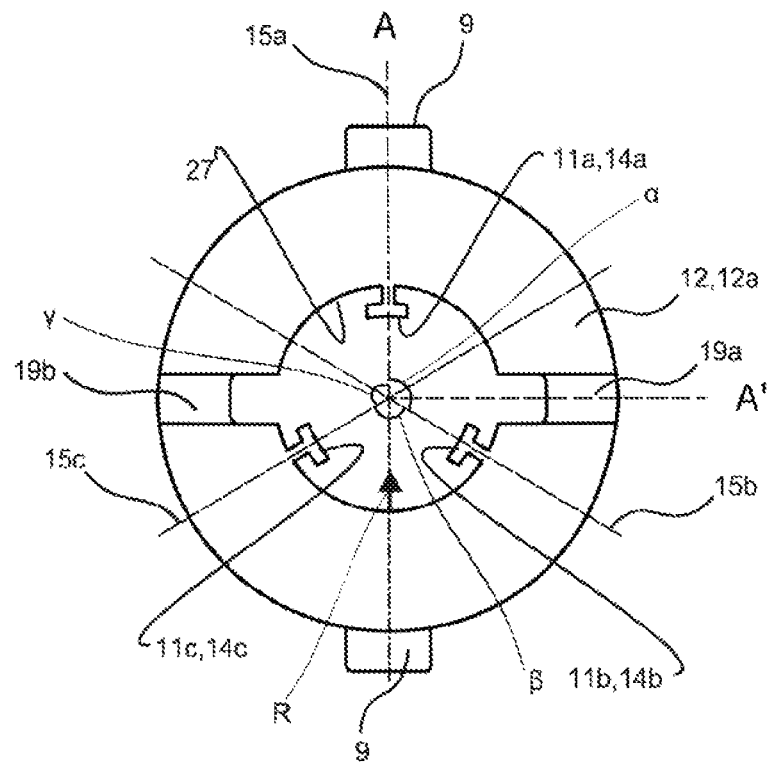
Figure 7:
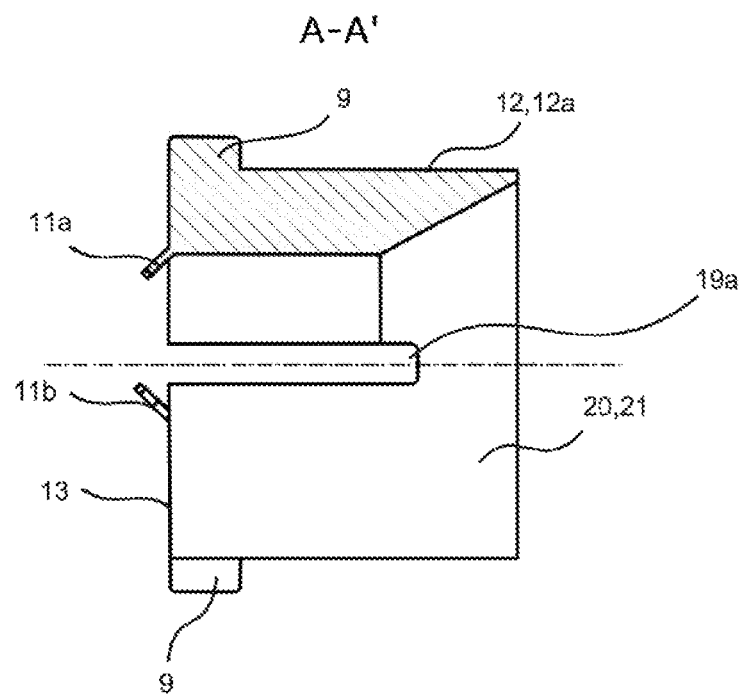
Figure 8:
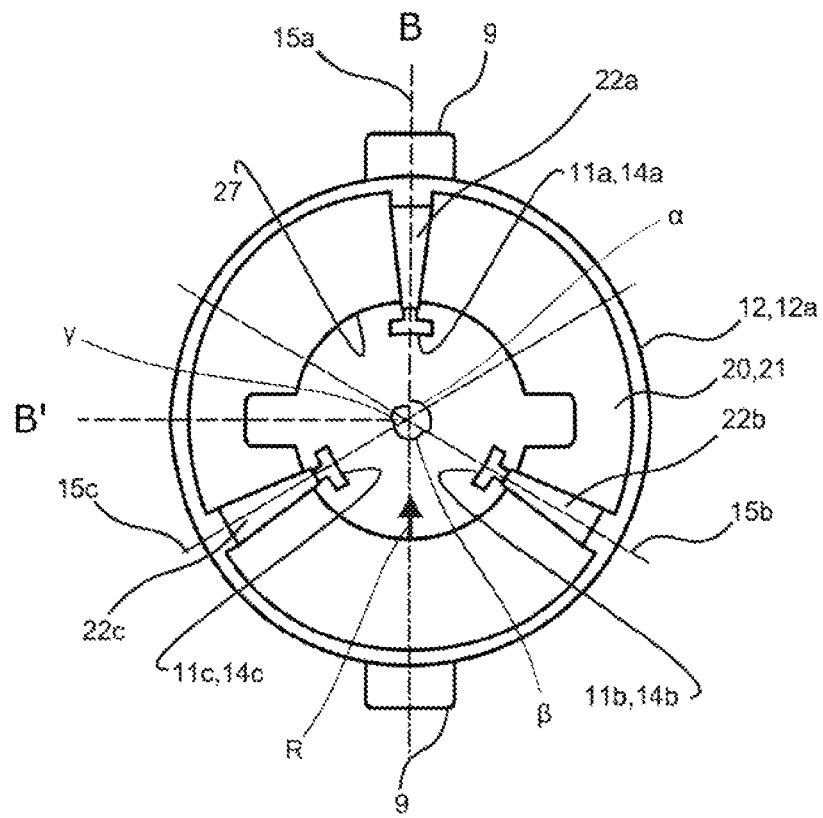
Figure 9:
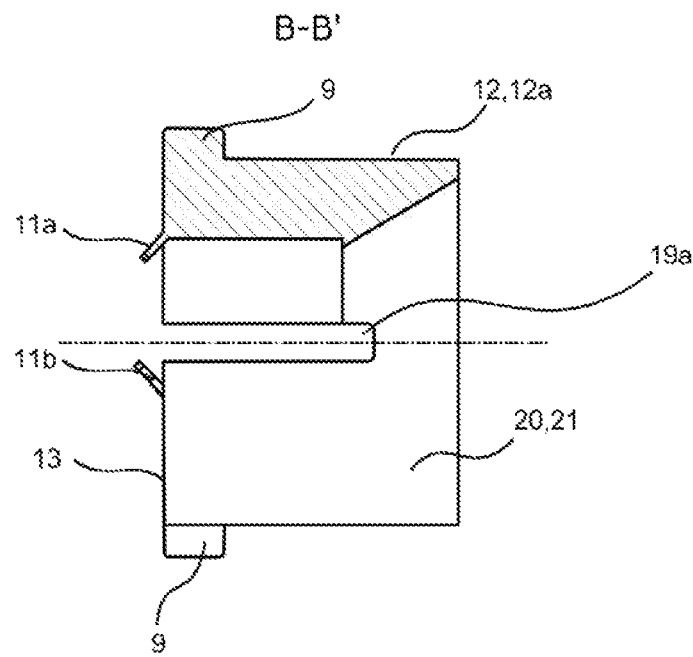

FIG. 4 is an isometric view of a collar element;
FIG. 5 is an isometric view of a collar element;
FIG. 6 is a plan view of a collar element;
FIG. 7 is a sectional view of a collar element;
FIG. 8 is a rear view of a collar element;
FIG. 9 is a sectional view of a collar element.

Figure 1:
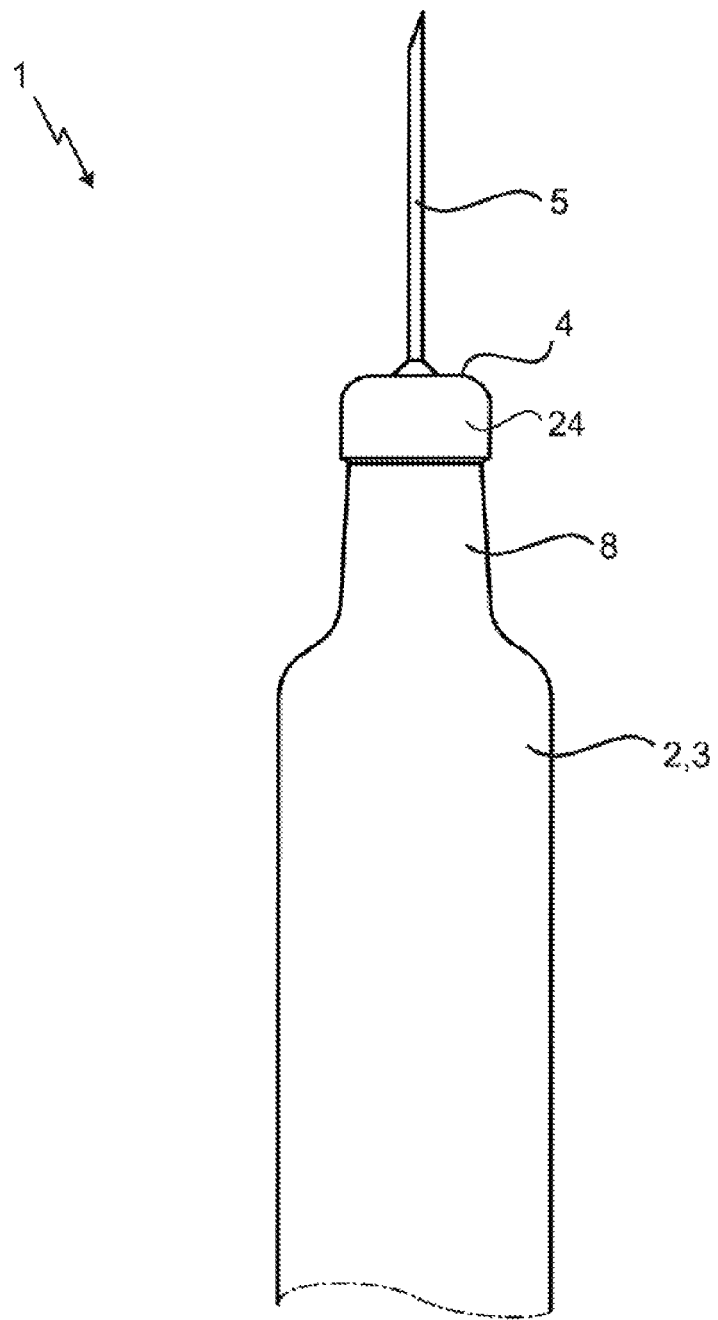
FIG. 1 shows a portion of a syringe without a safety device.

FIG. 1 shows a portion of a syringe (2) without a safety device (1). The syringe comprises a syringe body (3) which is designed as a hollow circular cylinder. The syringe body has a distal end region (8) comprising a distal end (4). Arranged at the distal end (4) is a piercing means (5). This piercing means (5) is connected via a hole in the distal end region (8) to the cavity of the syringe body (3), so that the medium to be injected during application of the syringe (2) can emerge through the piercing means (5). The distal end region (8) is designed as a conical end piece which has a smaller external diameter than the syringe body (3). The syringe also has a transition region (25) in which the external diameter of the syringe body merges into the external diameter of the end piece. Moreover, a projection (24) is arranged at the distal end region.

Figure 2:
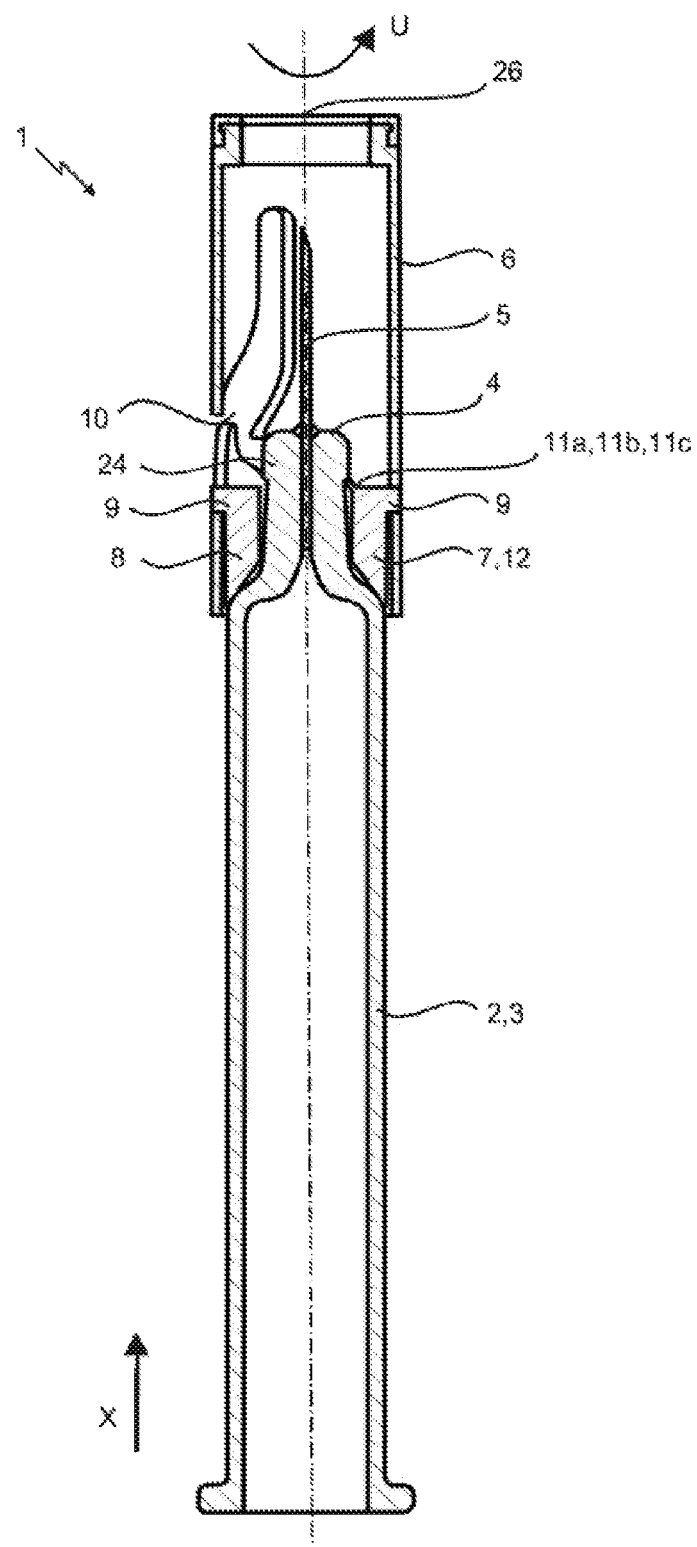
FIG. 2 is a sectional view of a syringe comprising a safety device.
Figure 3:
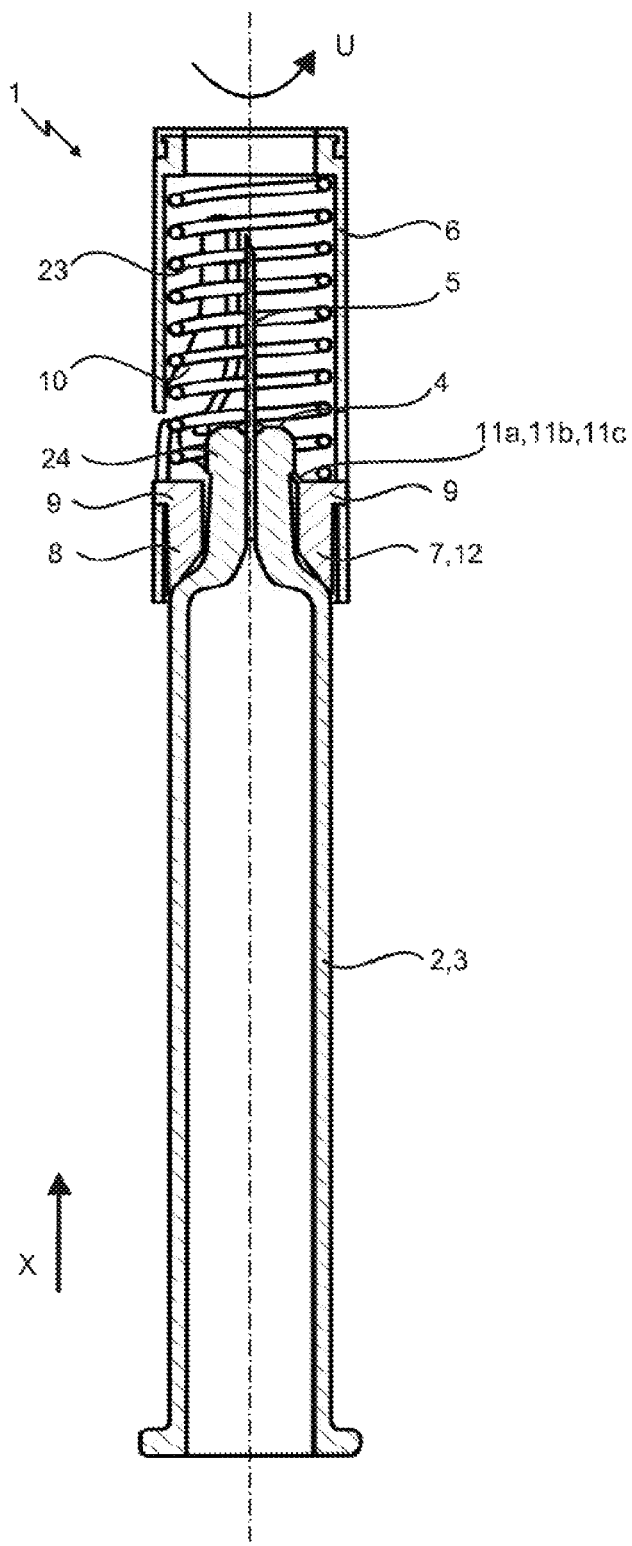
FIG. 3 is a sectional view of a syringe comprising a safety device.

FIG. 2 and FIG. 3 show a syringe comprising a safety device (1) for avoiding stab wounds. The syringe (2) comprises a syringe body (3) and a piercing means (5) arranged at the distal end (4) of the syringe body (3). The safety device (1) comprises a sleeve element (6), which extends along an axial direction (X) and at least partially encloses the piercing means (5) and the syringe body (3), and a collar element (7), which is arranged on a distal end region (8) of the syringe body (3) and locks the safety device (1) in the axial direction (X). The locking in the axial direction (X) is made possible by a projection (24) or a thicker portion at the distal end (4) of the syringe body, on which projection or thicker portion the distal end of the collar element rests.

The collar element (7) comprises two guide projections (9), which are each guided substantially in the axial direction (X) in a guide track (10) of the sleeve element (6) when the syringe body (3) is moved relative to the sleeve element (6). The collar element (7) is arranged on the distal end region (8) of the syringe body (3) so as to be rotatable in a circumferential direction (U) and has at least one tolerance compensating element (11a, 11b, 11c) which is in operative contact, mechanically, with the syringe body (3) so that tolerances of the syringe body (3) can be compensated for.

FIG. 3 again shows a safety device (1), which comprises a spring element (23) in the form of a spiral spring, which is operatively connected to the syringe body (3) and counteracts the movement of the sleeve element (6) relative to the safety device (1). Accordingly, the piercing means (5) remains inside the sleeve element (6) until the intended use. During use, the sleeve element (6) has to be moved counter to the spring force in order for the piercing means (5) to be able to pass through an opening (26) of the sleeve element (6). After the syringe (2) has been used, the sleeve element (6) automatically slides over the piercing means (5) again, driven by the spring force of the spring element (23). The guidance of the guide projection (9) in the guide tracks (10) causes the collar element (7) to rotate counter to the circumferential direction (U). The user is thus protected from receiving stab wounds from the used and contaminated piercing means.

FIG. 4 and FIG. 5 are each isometric views of the collar element (7), the distal end of the collar element (7) being shown in FIG. 4 and the proximal end of the collar element (7) being shown in FIG. 5. Furthermore, FIG. 6 is a plan view of the distal end of the collar element (7), and FIG. 8 is a plan view of the proximal end of the collar element (7).

FIGS. 7 and 9 are sectional views along the axes A-A' (in FIG. 6) and B-B' (in FIG. 8).

The collar element (7) is substantially formed as a hollow circular cylinder (12). The circular cylinder (12) comprises a lateral surface (12a), on which two guide projections (9) are arranged. The guide projections extend radially outwards from the lateral surface (12a), and are diametrically opposed to one another. Furthermore, said guide projections are formed as circular cylinders or as pins.

The collar element (7) comprises a proximal region (20) that has an inside taper (21). This can be seen in FIG. 5. Three protruding elements (22a, 22b, 22c) are arranged in this proximal region (20) of the collar element (7), which elements extend inwardly in the radial direction (R), from the collar element (7). The three protruding elements (22a, 22b, 22c) rest on the syringe body in the transition region (25) thereof, providing a further bearing point of the collar element (7) on the syringe body (3). This can be seen in FIGS. 5 and 8. Accordingly, just a small surface rests on the syringe body (3), and this reduces the friction between the collar element (7) and the syringe body (3) during rotation of the collar element (7).

The collar element (7) further comprises a distal region (18) in which the wall of the collar element (7) comprises at least two slots (19a, 19b) that extend in the axial direction (X). These slots additionally extend in portions in the proximal region (20) of the collar element (7), which region has the inside taper (21). The slots (9) allow better adaptation of the collar element (7) to different syringe bodies (3) and/or more simple attachment of the collar element (7) to the syringe body (3). The collar element (7) is usually pushed over the distal end (4) of the syringe body. This distal end (4) comprises a projection (24) or a thicker portion. The slots (9) make it possible for the collar element (7) to be widened during attachment, as a result of which said element can be more easily pushed over the projection (24).

The collar element (7) further comprises three tolerance compensating elements (11a, 11b, 11c). The tolerance compensating elements (11a, 11b, 11c) are arranged on the distal end (13) of the collar element (7) such that the central axes (15a, 15b, 15c) thereof in each case enclose an angle $\alpha=\beta=\gamma=120°$ relative to one another. This can be seen in FIG. 6 and FIG. 8, which are plan views of the distal end of the collar element (7).

FIG. 7 is a further sectional view along the axis A-A' from FIG. 6. Finally, FIG. 9 is a sectional view along the axis B-B' from FIG. 8. Furthermore, the tolerance compensating elements (11a, 11b, 11c) are formed integrally with the collar element (7).

The tolerance compensating elements (11a, 11b, 11c) extend inwardly in the radial direction (R), from the collar element (7), and thus protrude into the cavity of the circular cylinder (12), ensuring ideal positioning of the collar element (7) in the radial direction (R).

Furthermore, the tolerance compensating elements (11a, 11b, 11c) are formed in the manner of a punch. The punch-like tolerance compensating elements (11a, 11b, 11c) comprise a contact surface (12a, 12b, 12c) which can be brought into operative contact with the syringe body (3). These contact surfaces (12a, 12b, 12c) extend in a circumferential direction of the inner circle (27) of the hollow cylindrical collar element (7).

The at least one tolerance compensating element (11a, 11b, 11c) protrudes beyond a distal end (13) of the collar element (7) along the axial direction (X), ensuring ideal positioning of the collar element in the axial direction. This can be seen in FIG. 7 or FIG. 9, respectively.

All of the features disclosed in the application documents are claimed to be essential to the invention provided that they are novel over the prior art, either on their own or in combination with one another.

LIST OF REFERENCE SIGNS 1 safety device
2 syringe
3 syringe body
7 distal end of the syringe body
5 piercing means
6 sleeve element
7 collar element
8 distal end region of the syringe body
9 guide projection
10 guide track
11a, 11b, tolerance compensating element
11c tolerance compensating element
12 hollow circular cylinder
12a lateral surface of the circular cylinder
13 distal end of the collar element
14a, 14b contact surface
14c contact surface
15a, 15b, central axes of the tolerance compensating elements
15c central axis of the tolerance compensating elements
18 distal region of the collar element
19a, 19b slots
20 proximal region of the collar element
21 inside taper
22a, 22b protruding element
22c protruding element
23 spring element
24 projection
25 transition region
26 opening of the sleeve element
27 inner circle of the hollow cylindrical collar element
X axial direction
U circumferential direction
R radial direction
α, β, γ angle

The invention claimed is:

1. A safety device for avoiding stabwounds for a syringe having a syringe body and a piercing means arranged at the distal end of the syringe body, the safety device comprising a sleeve element, which extends along an axial direction (X) and at least partially encloses the piercing means and the syringe body, and a collar element, which is arranged on a distal end region of the syringe body and locks the safety device in the axial direction (X), the collar element comprising at least one guide projection, which is guided in at least one guide track of the sleeve element, substantially in the axial direction (X), when the syringe body is moved relative to the sleeve element, wherein:
the collar element is arranged on the distal end region of the syringe body, wherein the movement of the syringe body relative to the sleeve element causes the collar element to rotate in the circumferential direction (U) of the syringe body on account of the guidance of the guide projection in the at least one guide track of the sleeve element, and
wherein the collar element has at least one resilient tolerance compensating element which is in operative contact, mechanically, with the syringe body so that tolerances of the syringe body can be compensated for by deformation of the at least one tolerance compensation element.

2. The safety device according to claim 1, wherein:
the collar element is substantially formed as a hollow circular cylinder, the circular cylinder comprising a lateral surface, on which the at least one guide projection is arranged.

3. The safety device according to claim 1, wherein:
the at least one tolerance compensating element protrudes beyond a distal end of the collar element along the axial direction (X).

4. The safety device according to claim 1, wherein:
the at least one tolerance compensating element extends inwardly along the radial direction (R), from the collar element.

5. The safety device according to claim 1, wherein:
the at least one tolerance compensating element is formed in a manner of a punch, the tolerance compensating element comprising a contact surface which can be brought into operative contact with the syringe body.

6. The safety device according to claim 1, wherein:
the collar element comprises three tolerance compensating elements, the tolerance compensating elements being arranged on the distal end of the collar element such that two central axes of the tolerance compensating elements in each case enclose an angle (α, β, γ).

7. The safety device according to claim 1, wherein:
the at least one tolerance compensating element is formed integrally with the collar element.

8. The safety device according to claim 1, wherein:
the collar element comprises a distal region in which the wall of the collar element comprises at least two slots that extend in the axial direction (X).

9. The safety device according to claim 1, wherein:
the collar element comprises a proximal region that has an inside taper.

10. The safety device according to claim 9, wherein:
at least one protruding element is arranged at least in the proximal region of the collar element, the protruding element extending inwardly in the radial direction (R), from the collar element.

11. The safety device according to claim 1, wherein:
the safety device comprises at least one spring element, which is operatively connected to the syringe body and counteracts the movement of the sleeve element relative to the safety device.

12. The safety device according to claim 1, wherein:
the collar element and/or the at least one tolerance compensating element consists of slip-modified polyoxymethylene (POM) or of a silicone compound.

13. The safety device according to claim 1, wherein:
the collar element and/or the at least one tolerance compensating element comprise a glide-enhancing coating.

14. A safety device for avoiding stab wounds for a syringe having a syringe body and a piercing means arranged at the distal end of the syringe body, the safety device comprising a sleeve element, which extends along an axial direction (X) and at least partially encloses the piercing means and the syringe body, and a collar element, which is arranged on a distal end region of the syringe body and locks the safety device in the axial direction (X), the collar element comprising at least one guide projection, which is guided in at least one guide track of the sleeve element, substantially in the axial direction (X), when the syringe body is moved relative to the sleeve element, wherein:

the collar element is arranged on the distal end region of the syringe body so as to be rotatable in a circumferential direction (U) and has at least one tolerance compensating element which is in operative contact, mechanically, with the syringe body so that tolerances of the syringe body can be compensated for the movement of the syringe body relative to the sleeve element causing the collar element to rotate in the circumferential direction (U) on account of the guidance of the guide projection in the at least one guide track of the sleeve element, wherein the at least one tolerance compensating element protrudes beyond a distal end of the collar element along the axial direction (X).

15. The safety device according to claim 14, wherein:
the at least one tolerance compensating element is formed in a manner of a punch, and
the tolerance compensating element comprising a contact surface which can be brought into operative contact with the syringe body.

16. The safety device according to claim 14, wherein:
the collar element comprises a distal region in which the wall of the collar element comprises at least two slots that extend in the axial direction (X).

17. A safety device for avoiding stab wounds for a syringe having a syringe body and a piercing means arranged at the distal end of the syringe body, the safety device comprising a sleeve element, which extends along an axial direction (X) and at least partially encloses the piercing means and the syringe body, and a collar element, which is arranged on a distal end region of the syringe body and locks the safety device in the axial direction (X), the collar element comprising at least one guide projection, which is guided in at least one guide track of the sleeve element, substantially in the axial direction (X), when the syringe body is moved relative to the sleeve element, wherein:
the collar element is arranged on the distal end region of the syringe body so as to be rotatable in a circumferential direction (U) and has at least one tolerance compensating element which is in operative contact, mechanically, with the syringe body so that tolerances of the syringe body can be compensated for the movement of the syringe body relative to the sleeve element causing the collar element to rotate in the circumferential direction (U) on account of the guidance of the guide projection in the at least one guide track of the sleeve element, and
wherein the collar element comprises three tolerance compensating elements, the tolerance compensating elements being arranged on the distal end of the collar element such that two central axes of the tolerance compensating elements in each case enclose an angle ($\alpha$, $\beta$, $\gamma$).

18. The safety device according to claim 17, wherein:
the collar element comprises a distal region in which the wall of the collar element comprises at least two slots that extend in the axial direction (X).

19. The safety device according to claim 17, wherein:
the collar element comprises a proximal region that has an inside taper, wherein the at least one tolerance compensating element extends inwardly along the radial direction (R), from the collar element.

20. The safety device according to claim 17, wherein:
the safety device comprises at least one spring element, which is operatively connected to the syringe body and counteracts the movement of the sleeve element relative to the safety device.

* * * * *